(12) United States Patent
Miyoshi et al.

(10) Patent No.: US 10,042,014 B2
(45) Date of Patent: Aug. 7, 2018

(54) APPARATUS AND METHOD FOR ANALYZING SAMPLES WITH NMR

(71) Applicants: Bridgestone Corporation, Chuo-ku (JP); The University of Akron, Akron, OH (US)

(72) Inventors: Toshikazu Miyoshi, Akron, OH (US); Michael C. Davis, Independence, OH (US); Jiahuan Hu, Akron, OH (US)

(73) Assignees: Bridgestone Corporation, Chuo-ku (JP); The University of Akron, Akron, OH (US)

(*) Notice: Subject to any disclaimer, the term of this patent is extended or adjusted under 35 U.S.C. 154(b) by 206 days.

(21) Appl. No.: 15/132,903

(22) Filed: Apr. 19, 2016

(65) Prior Publication Data

US 2016/0305896 A1    Oct. 20, 2016

Related U.S. Application Data

(60) Provisional application No. 62/149,905, filed on Apr. 20, 2015.

(51) Int. Cl.
    *G01V 5/00*      (2006.01)
    *G01R 33/30*     (2006.01)
    *G01N 24/08*     (2006.01)

(52) U.S. Cl.
    CPC ............ *G01R 33/30* (2013.01); *G01N 24/08* (2013.01); *G01R 33/307* (2013.01)

(58) Field of Classification Search
    CPC ....... G01R 33/30; G01R 33/307; G01N 24/08
    USPC ................................ 324/321, 310, 308, 309
    See application file for complete search history.

(56) References Cited

U.S. PATENT DOCUMENTS

| 5,760,586 | A  | * | 6/1998 | Foerster | ............... | G01R 33/307 |
| | | | | | | 324/318 |
| 7,497,129 | B2 | * | 3/2009 | Kimura | .................. | G01N 24/08 |
| | | | | | | 73/842 |
| 2015/0268314 | A1 | * | 9/2015 | Peterson | .............. | G01R 33/305 |
| | | | | | | 324/321 |

* cited by examiner

*Primary Examiner* — Reena Aurora
(74) *Attorney, Agent, or Firm* — Meredith E. Hooker; J. Gregory Chrisman (57) ABSTRACT

An apparatus and method for testing and analyzing the molecular structure of a sample material in an NMR device are described. A sample is held in a pre-determined stretched state in an apparatus that includes the sample arranged between two body components that are secured together with one or more retaining members that fit around the bodies or portions thereof. The apparatus is inserted into an NMR device to obtain NMR spectrums for analyzing the molecular structure of the samples, for instance, identifying strain-induced crystallinity and quantifying the same at pre-determined stretch ratios of a sample material.

28 Claims, 5 Drawing Sheets

APPARATUS AND METHOD FOR ANALYZING SAMPLES WITH NMR

This application claims the benefit of U.S. provisional application Ser. No. 62/149,905 filed Apr. 20, 2015, the contents of which are incorporated herein in their entirety by reference.

TECHNICAL FIELD

The present invention relates to an apparatus and method for analyzing a sample by NMR, and more particularly, an apparatus and method for obtaining solid-state NMR spectra for an elongated or stretched elastomeric or rubber-containing sample.

BACKGROUND

Materials having elastic properties, such as elastomers, are desirable in industry for their ability to resume an original shape after deformation or elongation. These materials are used in a wide range of industries and have many applications, such as, tires, belts, gaskets, gloves and foams. One example of an elastomer is natural rubber. Natural rubber represents a limited renewable source and thus other synthetic rubbers are manufactured to meet demands. The performance of elastomers, such as natural rubber and synthetic rubber, under mechanical stresses, such as stretching and elongation, is important to their ability to perform a desired function. Thus, the study of elastomers under mechanical stresses, and the data therefrom, provides valuable information for the selection of the materials for certain uses. For example, the viscoelastic properties of rubber materials directly relate to the bulk properties, e.g., rolling resistance, wet traction, of automobile tires and therefore understanding the viscoelasticity and the structure of rubber materials, which include various kinds of fillers, under deformation is important in developing new tire technology with desirable properties.

For instance, the ability of natural rubber to exhibit strain-induced crystallization has been the basis of studies. To measure strain-induced crystallinity, techniques such as wide angle X-ray diffraction (WAXD) and nuclear magnetic resonance (NMR) have been utilized. Diffraction based techniques suffer from the disadvantage that select amorphous peaks are not easily observed in high resolution alongside crystalline peaks over a range of elongation ratios. Obtaining high resolution in solid state NMR spectra generally requires rotating a sample at a frequency of several kHz and prior disclosures teach rubber ring samples being stretched over a post and rotated. Stretching rubber rings over a post presents drawbacks such as significant stretching errors, inaccurate data, and a limited maximum stretching ratio.

There remains a need for an apparatus that can accommodate elastomer samples for solid-state NMR testing such that the samples can be stretched at multiple elongation ratios up to the stretching limits of the material. The method described herein provides a robust process of stretching samples and obtaining data that can be used to evaluate the molecular structure and molecular motion of a sample, such as identifying the formation and amount of strain-induced crystalline material.

SUMMARY

Provided herein is an apparatus for testing and gathering data of a sample with an NMR device. The apparatus includes a first body and a second body for holding a sample such that the sample is arranged in the apparatus between the first and second bodies. The apparatus can further include a retaining member for securing the sample between the first body and the second body. The retaining member can fit around an outer surface or portion of the first and second bodies to prevent the bodies from moving apart during testing, such as rotating in an NMR device.

The sample can be any suitable material, for example, the sample can be an elastomer or contain rubber, natural rubber or synthetic rubber. In one embodiment, the sample can be a stretched material. The stretched sample can have a stretch ratio in the range of 1 to 10, for example greater than 4.

In another embodiment, the sample arranged between the first and second bodies can be in direct contact with the bodies such that no other materials are present between the sample and the bodies.

The components of the apparatus, for example the bodies and retaining member or members, can be made of any suitable material, and preferably a material with a low carbon background. The material of construction of the components can be plastic or thermoplastic.

In an embodiment, the retaining member can be positioned around an end portion of the first body and an end portion of the second body. The retaining member can further be positioned around a portion of the sample arranged between the first and second body, for instance, between the end portions of the bodies.

In another embodiment, the retaining member can be positioned around the first and second bodies and extend around the entire length of the bodies to surround the entire elongate portions of the bodies and outer surface facing away from the sample.

The apparatus can further include a second retaining member. The second retaining member can be positioned around an end portion of the first body and an end portion of the second body. The first retaining member and the second retaining member can be removably fixed to the first body and the second body.

The apparatus is preferably designed to be symmetrically balanced for rotating the sample at frequencies of more than 0.5 kHz and up to 10 kHz. For example, the components, such as the bodies and retaining members, can have the same shape and the same dimensions or be symmetrical to one another.

In another embodiment, the first and second bodies can have an elongate portion having a sample contact surface. The sample contact surface of the first body and the second body can be in direct contact with the sample, for example, respectively in contact with opposing surfaces of the sample.

The apparatus can be inserted into the sample receiving space of a NMR device, for instance the apparatus being inserted into a solid state rotor, for rotating and analyzing the sample in a magnetic field. For example, a solid state NMR spectrum of the sample can be measured and obtained while the sample is rotated in the NMR device. The apparatus containing the sample can be rotated in the NMR device at a frequency range of 2 to 10 kHz. The sample can be positioned in the apparatus such that the sample is rotated parallel to the axis of rotation. Because the sample is arranged in the apparatus in a vertically stretched direction, rotation of the sample along the axis of rotation is easily achievable.

In another embodiment, a method for analyzing the molecular structure or molecular motion of a sample is described. The method can include introducing an apparatus containing a sample into a sample receiving of an NMR device; the sample being arranged (e.g., vertically) between a first body and a second body of the apparatus. Another step of the method is rotating the apparatus containing the sample in the NMR device, for example in the range of 1 to 10 kHz, and obtaining an NMR spectrum of the sample and using the position of peaks at an indicative resonance shift in the NMR spectrum to elucidate the molecular structure or molecular motion of the sample.

In an embodiment, the sample can be rotated in the NMR device at an angle equal to the magic angle of 54.74° with respect to the direction of the external magnetic field in order to average unwanted contributions to the NMR spectrum from anisotropic interactions and detect and obtain a NMR spectrum that can be interpreted to glean structural information related to the sample.

As noted above, the sample used in the method can be any suitable material, for example, the sample can be an elastomer or contain rubber, natural rubber or synthetic rubber. In one embodiment, the sample can be a stretched material. The stretched sample can have a stretch ratio in the range of 1 to 10, for example greater than 4.

In another embodiment, the method further includes the step of identifying strain-induced crystalline structure in the sample. The crystalline structure can be caused by the sample being stretched. A further step of quantifying the amount of strain-induced crystalline structure in the sample can be carried out.

The method can further include comparing the NMR spectrum of the sample to a reference NMR spectrum generated by obtaining a NMR spectrum of the sample in an upstretched state.

The apparatus used in the method can have the first body positioned against a first surface of the sample and the second body against a second surface of the sample. The apparatus can further include a first retaining member arranged over a portion of the first body and the second body and a second retaining member over a portion of the first body and the second body.

In another embodiment, the method can include using an apparatus having portions of a stretched sample being arranged within a first retaining member and a second retaining member.

The embodiments of this section may be provided alone or in combination with any one or more of the embodiments discussed above.

BRIEF DESCRIPTION OF THE DRAWINGS

FIG. 3A shows an unassembled portion of an apparatus including a first body and a second body having a sample positioned there between.

DETAILED DESCRIPTION

The terminology as set forth herein is for description of the embodiments only and should not be construed as limiting the invention as a whole.

Herein, when a range such as 5-25 (or 5 to 25) is given, this means preferably at least or more than 5 and, separately and independently, preferably not more than or less than 25. In an example, such a range defines independently at least 5, and separately and independently, not more than 25.

An apparatus for testing or analyzing a sample with an NMR device is described. The apparatus allows a user to utilize NMR data so that the molecular structure and the molecular motion of the sample, for instance a stretched rubber-containing sample, can be analyzed. The NMR spectrum for a sample, or series of samples, makes it possible to analyze the molecular structure of the sample with high accuracy and easily evaluate the molecular motion thereof by observing the changes in line width or formation of new peaks in the obtained spectrums over various stretching ratios. For example, spectrums can be compared for unstretched samples and stretched samples to evaluate the molecular motion and thereby evaluate the extent that a sample, e.g., an elastomer, is affected under strain or tension. Understanding the properties of samples while in a stretched state can assist in the selection and development of materials to improve breaking strength and prevent crack formation. Such analysis of samples can contribute to the design and selection of materials having reduced rolling resistance and increased gripping performance.

The apparatus, for example a kit or a sample holding device for a rotor insert, can be made of components that fit together to securely hold a sample for testing in the NMR device. The components can be made of any suitable material and, preferably, the components of an individual apparatus are made from the same material. For example, the components can be made of non-ferromagnetic materials or materials having a low carbon background that provide different $^{13}C$ chemical shifts from those of the sample material being tested so a solid-state NMR spectrum of the sample can be obtained. In one embodiment, the materials can be free of carbon or hydrogen such that a $^{13}C$ NMR spectrum or a $^1H$ NMR spectrum can be obtained. In another embodiment, the materials preferably result in peaks that do not overlap with the observed peaks for the sample being tested in order to generate $^{13}C$ NMR or a $^1H$ NMR spectra representative of the sample. Materials of construction for the components can include metals, e.g., aluminum, aluminum alloy, brass, brass alloys, titanium, titanium alloys, copper, copper alloys, zirconium, zirconium alloys, boron nitride, alumina, polymers, plastics, such as thermoplastics, e.g., poly(tetrafluoro ethylene) (PTFE), poly(oxymethylene) (POM), and combinations thereof.

Any suitable sample can be used with the apparatus. The sample can be, for example, an elastomer, rubber, natural rubber, synthetic rubber (e.g., isoprene rubbers) or a material containing the same or combinations thereof. Natural rubber is cis-1,4-polyisoprene and can be obtained as latex from a large variety of plants in many regions of the world.

The sample can be tested in the apparatus in a stretched or unstretched state. In a stretched state, for example, the sample can have elongation or stretch ratio, $\lambda$, in the range of 0.5 to 10 and above. The stretch ratio is limited by the elastic properties of the material. In an example, the sample can have a stretch ratio ($\lambda$) in the range of 1 to 8, or above or greater than 2, 3, 4, 5, 6 or 7 or more. A pre-determined stretch ratio of a sample can be achieved with the use of conventional equipment, for example, with an Instron machine, so it is possible to obtain, compare and investigate NMR spectrums and analyze the molecular structure and molecular motion of samples at various stretch ratios. Samples can be prepared as needed for the particular stretching device used. For instance, a sample can be formed or cut into an ASTM dumbbell shape prior to stretching.

Figure 1:
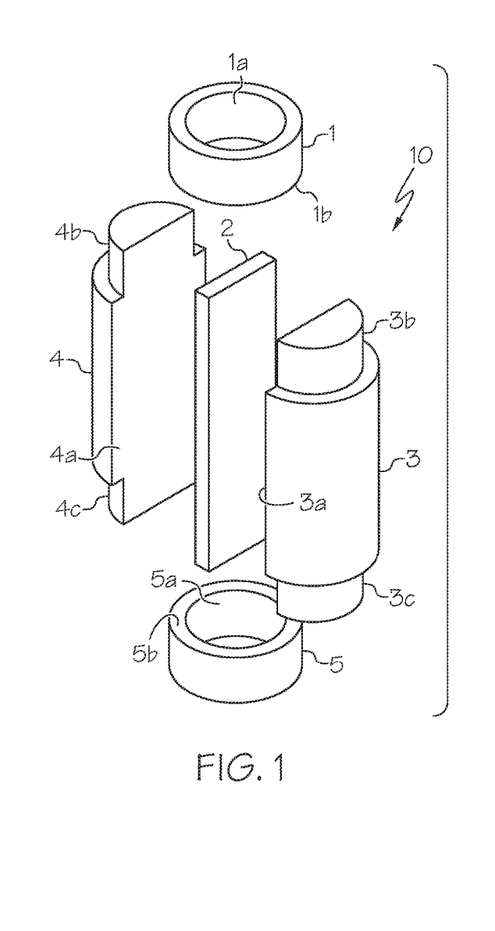
FIG. 1 shows an exploded view of an apparatus containing a sample. The apparatus is used for testing the sample in the solid state with an NMR device.

FIG. 1 shows a disassembled apparatus for testing a sample with an NMR device. The apparatus 10 contains a first body 3 and a second body 4 for holding a sample 2 there between. As shown, the first body 3 and the second body 4 can be symmetric to one another and have the same shape and dimensions and the bodies 3, 4 provide a uniform, well balanced sample-holding body when securing a sample for being tested in an NMR device. The first body 3 and the second body 4 have a sample contact surface 3a, 4a for directly contacting the sample 2 to secure it in the apparatus 10. The sample contact surfaces 3a, 4a are preferably uniform and flat along one side of the bodies 3, 4. The entire sample contact surfaces 3a, 4a can be in contact with sample 2 or, alternatively, a portion of either surface 3a, 4a can contact the sample during testing.

Figure 2A:
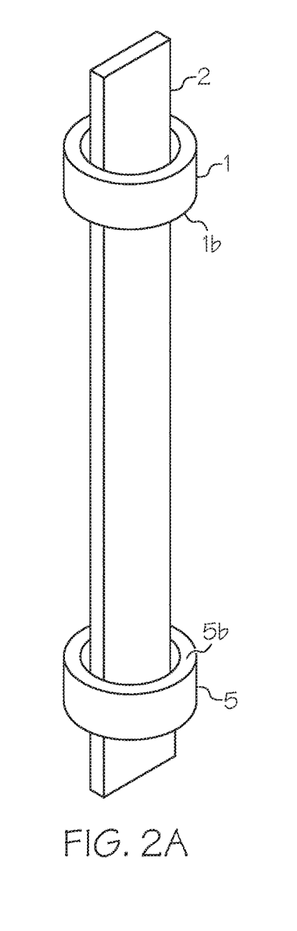
FIG. 2A shows a sample stretched within two retaining members of an apparatus.
Figure 2B:
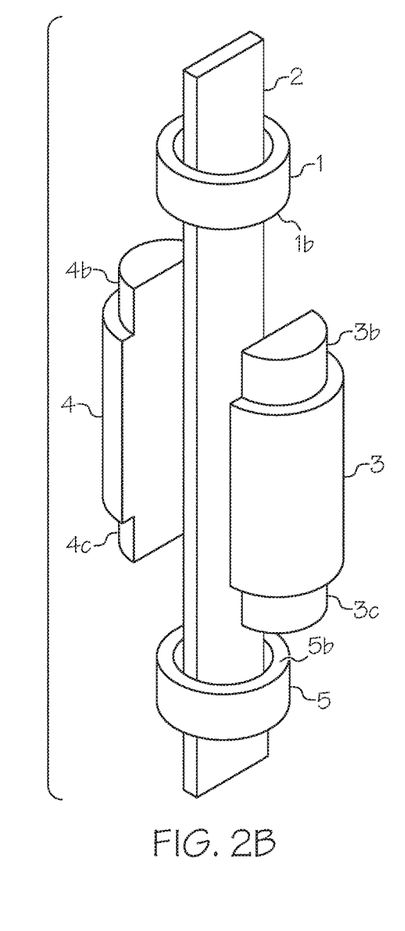
FIG. 2B shows the sample of FIG. 2A having a first body and a second body arranged around opposing surface portions of the sample.
Figure 2C:
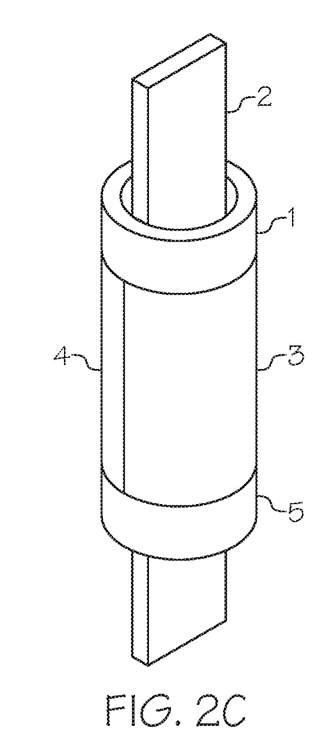
FIG. 2C shows the retaining members positioned over the end portions of the first and second bodies to secure a sample between the bodies.
Figure 2D:
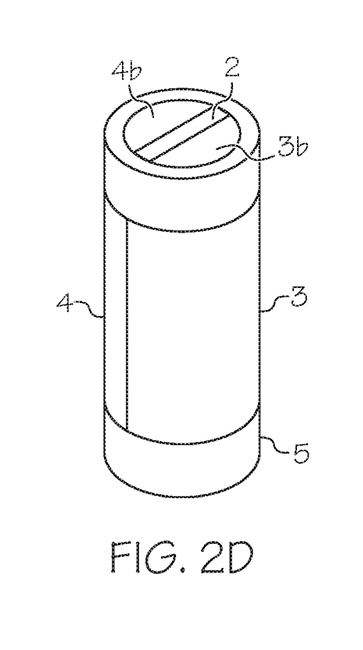
FIG. 2D shows the apparatus of FIG. 2C having the excess sample material removed at each end of the apparatus.

The sample can have a general rectangular shape as shown with a first contact surface and a second contact surface opposing one another and facing the sample contact surfaces 3a, 4a of the first and second bodies 3, 4. Sample material extending beyond the sample contact surfaces 3a, 4a or outside the outer perimeter of the surfaces 3a, 4a can be removed prior to testing, for example, the excess sample material can be cut off or removed with a blade. In one example, a sample 2 can be a stretched piece of elastomer or rubber-containing material that extends outward from each end of the first and second bodies 3, 4 as shown in FIGS. 2A-2C. Prior to testing the sample in an NMR device, the portions of the sample extending from both ends of the bodies 3, 4 is removed such that the edges of the entire sample 2 facing perpendicular to the sample contacting surfaces 3a, 4a of the bodies 3, 4 are flush with or recessed from the outer perimeter of the surfaces 3a, 4a.

The first and second bodies 3, 4 press against the sample 2 such that the sample cannot move or slide about the apparatus during testing or rotating at high speeds. For example, the bodies 3, 4 secure the sample in an unstretched state, stretched state or at a pre-determined stretch ratio to prevent the sample 2 from retracting or returning to its pre-stretched or unstretched shape. Thus, the apparatus 10 retains a sample at a fixed stretch ratio throughout a testing period in an NMR device.

In one embodiment, the sample 2 is secured between the first body 3 and the second body 4 with the use of a retaining member. For example, FIG. 1 shows a first retaining member 1 and a second retaining member 5. The retaining members 1, 5 can have a ring shape with a center opening, e.g., circular, for accommodating a portion of the sample 2 and end portions, e.g., 3b, 4b, of the first and second bodies 3, 4. As show, the retaining members 1, 5 have an inner ring surface 1a, 5a that defines the center opening space and a face surface 1b, 5b for resting against a section of the elongate portion of the bodies 3, 4 located between the two end portions. The diameter of the center opening of each retaining member is slightly greater that the diameter of two end portions placed together to accommodate for the presence of a sample arranged between the two end portions. The retaining member 1, 5 should fit tightly around the end portion of the bodies to provide a secure interlocked apparatus that can be stably rotated in an NMR device.

The retaining members 1, 5 can be positioned to fit around the end portions, e.g., 3b, 4b, such that the inner ring surface 1a, 5a is in direct contact with the end portions to secure the bodies 3, 4 together and retain the sample 2 there between. As positioned around the end portions, the retaining members 1, 5 are also positioned around a portion of the sample 2 that is arranged between the bodies 3, 4. The inner ring surface 1a, 5a of the retaining members may be in contact with the sample, for instance, the portion of the sample 2 between the two end portions, e.g., 3c, 4c, at the perimeter edge. Preferably, the end surface of the retaining members 1, 5 that faces away from the elongate portion of the bodies 3, 4 is flush with the end portions of the bodies to form a flat end surface at each end of the apparatus 10.

The first and second retaining members 1, 5 can be positioned around the end portions of the bodies 3, 4 by sliding the members over the ends of the bodies having a sample retained there between. The apparatus 10 is designed so the retaining members 1, 5 are removably fixed to the first body and the second body such that the sample 2 can be replaced with a new sample for additional testing. The first and second retaining members 1, 5 can be interchangeable and either member can be positioned around either end portions of the bodies 3, 4. The first and second retaining members 1, 5 can be symmetric and have the same shape and dimensions so the members 1, 5 provide a uniform, well balanced apparatus when securing a sample between the bodies for testing in an NMR device.

FIGS. 2A-2E show a method for loading an apparatus 10 with a sample 2 for analyzing the molecular structure and molecular motion of the sample with an NMR device. A sample 2, in a stretched or unstretched state, extends through a first and second retaining member 1, 5. In an example, a sample in an unstretched state can be positioned through two retaining members, e.g., 1, 5, and then stretched to a pre-determined stretch ratio, $\lambda$, while the retaining members remain positioned around a portion of the sample as shown in FIGS. 2A-2B. A first and second body 3, 4 can be positioned on opposing sides of the sample 2 at a point between the retaining members 1, 5. The sample contact surfaces 3a, 4a of the bodies 3, 4 are clamped, pressed or arranged against the sample, for example, as it is held at a select stretch ratio. Excess or residual sample material extending from the perimeter of the bodies 3, 4 can be removed, for example, by using a razor.

To secure the sample 2 between the first and second bodies 3, 4, the retaining members 1, 5 are slid over the end portions of the bodies 3, 4. In this arrangement, the inner ring surfaces 1a, 5a that define the center openings of the members contact the outer surface of the end portions and prevent the bodies 3, 4 from separating and being in contact with the sample 2. As shown, the height of the retaining members 1, 5 can be the same as the length of the end portions of the bodies 3, 4. The end surface of the retaining members 1, 5 can be flush with the ends of each end portion to form flat end faces on both ends of the apparatus 10.

Figure 2E:
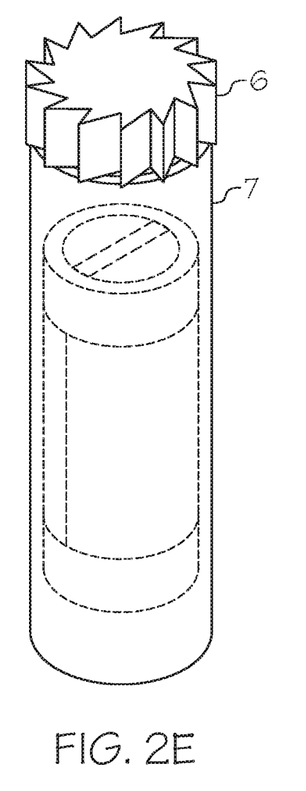
FIG. 2E shows the apparatus in a NMR sample tube or rotor insert for rotating the apparatus and sample contained therein in an NMR probe for testing the sample.

The assembled apparatus 10 can be inserted into a rotor insert or probe of an NMR device. Because the sample is held in the apparatus inside the rotor insert, it is possible to carry out a temperature-variable measurement by controlling the temperature inside rotor insert. As shown in FIG. 2E, the apparatus 10, having a cylindrical shape, can fit into a rotor insert tube 7. Preferably, the apparatus is slidably removable from the rotor insert 7. The rotor insert 7, as shown, can be a tube having a circular opening space therein along its length and, optionally, a closed end.

A rotor gear 6 is positioned on the rotor insert 7 for engaging the rotor of an NMR device for rotating the apparatus 10 containing the sample 2. The length and width or diameter of the apparatus 10 is set to accommodate insertion into a sample receiving space of an NMR device or rotor insert of an NMR device. For example, the length of the apparatus 10 can be in the range of 6 to 15 mm or as suitable for insertion into an NMR device or rotor insert. The width of the apparatus 10 can be in the range of 2 to 6 mm or as suitable for insertion into an NMR device or rotor insert. As arranged in the rotor insert 7, the outer surface of the apparatus 10 can be in contact with the inner surface of the rotor insert to prevent the apparatus 10 from moving about the rotor insert 7 during testing in an NMR device. A tight fit of the apparatus 10 in the rotor insert 7 helps ensure the sample can be rotated in the NMR device stably over a testing period.

The rotor insert can be introduced into a sample receiving space of an NMR device. The NMR device is used to obtain an NMR spectrum of the sample, for instance, a solid-state, high-resolution $^{13}C$ NMR spectrum. An NMR spectrum of the sample can be obtained by rotating the apparatus and sample in the NMR device. The NMR spectrum can be used to elucidate molecular structure and molecular motion of the sample and identify the formation of peaks indicative of crystallinity in the material. For example, stretching a sample can lead to the formation of strain-induced material such as strain-induced crystalline structure in the sample. The data obtained from the NMR device and spectrum can be used to quantify the amount or percentage of material or structure formed (e.g., crystallinity) from stretching a sample and further identifies the stretching ratio needed to induce such formations. In another example, an obtained NMR spectrum of a sample can be compared to a reference NMR spectrum that was generated by testing and obtaining an NMR spectrum of the same material in a different state. For instance, a NMR spectrum for an unstretched sample can be used as a reference for comparison to the NMR spectrums for different stretch ratios of the same material in order to evaluate the stretch ratio at which molecular motion occurs, e.g., strain-induced crystalline structure and observe how molecular dynamic geometry changes as a function of stretching ratio.

To obtain an NMR spectrum for a sample, the apparatus 10 containing the sample can be rotated in the NMR device at a frequency in the range of 0.5 to 15 kHz, for example, from 1 to 10 kHz or 2 to 5 kHz, or at least 3, 4, 5 or 6 kHz. In certain instances, the apparatus 10 and sample are not rotated to collect data about the sample for analyzing the molecular structure of the sample.

The apparatus 10 containing the sample 2 can be rotated at any angle for purposes of gathering data for the sample, for example, an NMR spectrum. In one embodiment, the apparatus and sample are rotated at the magic angle of 54.74° with respect to the external magnetic field to measure an NMR spectrum and thereby the molecular structure of the sample 2 can be probed. The apparatus and sample can be rotated for a pre-determined period of time as desired, for example, in the range of 2 to 48 hours or 12 to 24 hours. Testing of the sample 2 can be at any temperature, for example, in the range of 20 to 30° C.

As shown in FIGS. 2A-2E, the sample 2 is positioned or stretched along or parallel to the rotor insert or probe rotation axis in the NMR device. With the stretching direction along the rotating axis, the stretching ratio is only limited by the inherent elastic properties of the sample. For example, a natural rubber sample can break at stretch ratios above 7.

Figure 3A:
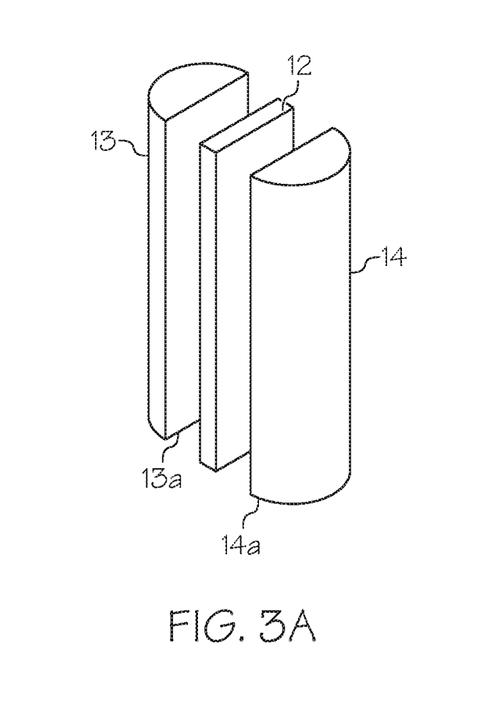
Figure 3B:
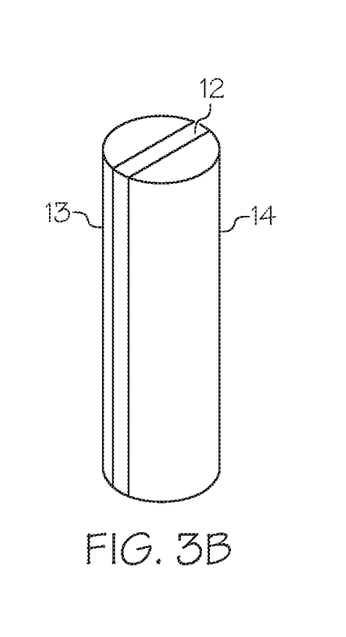
FIG. 3B shows a first body and a second body of an apparatus pressed against a opposing surfaces of a sample.
Figure 3C:
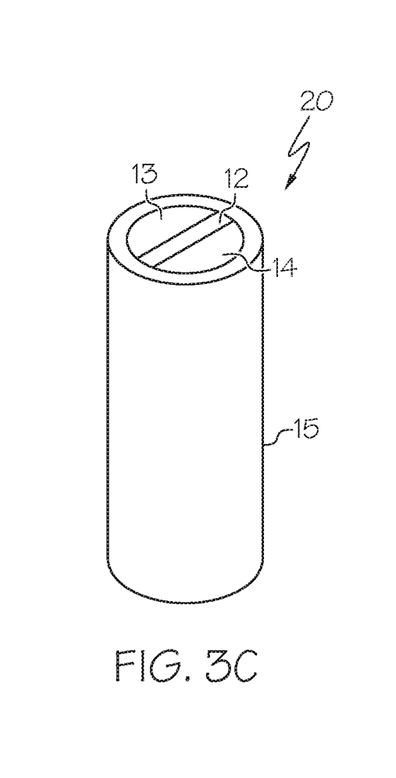
FIG. 3C shows an apparatus having a retaining member positioned around a first body and a second body to secure a sample there between. The apparatus is used for testing the sample in the solid state with an NMR device.

In another embodiment, FIGS. 3A-3C show an apparatus 20 for testing a sample with an NMR device. The apparatus 20 has a first body 13 and a second body 14 for holding a sample 12 there between. Preferably, the first and second bodies 13, 14 are symmetric and have the same shape and dimensions. As shown, the bodies 13, 14 have a sample contact surface, e.g., in the form of a flat surface that faces the sample, for directly contacting the sample 12 to secure it in the apparatus 20. The bodies can have a uniform semi-cylinder shape with a constant cross section area along the entire length of the bodies.

The sample 12 is arranged between the bodies 13, 14 such that no excess sample material protrudes or extends outward from the perimeter of either body 13, 14. In one example, the sample 12 fills the entire space between the bodies 13, 14 and is in direct contact with both bodies. Alternatively, the sample 12 can occupy a portion of the area between the bodies 13, 14 and thereby there may be void space between the bodies not filled with sample 12 material or any other material. The sample 12 can be loaded in the apparatus 20 and between the bodies 13, 14 as described above for apparatus 10. For instance, to test a stretched sample, the bodies 13, 14 can be clamped, pressed or arranged against opposing surfaces of a sample 12 to retain the sample in a pre-determined stretched or unstretched state. To secure the sample 12 between the bodies, a retaining member 15 can be positioned around the sample 12 and first and second bodies 13, 14.

The retaining member 15 is a tube having an opening to accommodate the first and second bodies 13, 14 and sample 12 arranged there between. In an example, the opening can extend the entire length of the member 15 or alternatively be closed at one end. The opening in the retaining member 15 is preferably sized to accommodate the entire length of the first and second bodies 13, 14 such that the retaining member 15 surrounds both bodies 13, 14 and the sample 12 along their entire length as shown. To secure the bodies together so the sample 12 does not move or slide about during testing, the retaining member 15 can contact the outer surface of each body 13, 14 as the sample 12 is tightly held. The top or end of the retaining member 15 is flush with the ends of the bodies 13, 14 and sample 12.

Although not shown, the assembled apparatus 20 including both bodies 13, 14, sample 12 and retaining member 15, can be inserted into a rotor insert or probe of an NMR device for testing the sample as described above for apparatus 10.

In order to demonstrate the practice of the present disclosure, the following examples have been prepared and tested. The examples should not, however, be viewed as limiting the scope of the present disclosure. Numerous variations over these specific examples are possible without departing from the spirit and scope of the presently disclosed embodiments.

EXAMPLE

Generation of NMR spectra for rubber-containing samples at pre-determined stretch ratios.

An apparatus as shown in FIG. 1 was used to test rubber-containing samples. The components of the apparatus were all made of polyoxymethylene polymer. The three rubber-containing samples had the following formulation in parts per rubber component (phr) as shown in Table 1 below.

TABLE 1

| Sample Material | Isoprene Rubber | Natural Rubber | Carbon Black | Sulfur | Stearic Acid | Zinc Oxide | Accelerator | Antioxidant |
| --- | --- | --- | --- | --- | --- | --- | --- | --- |
| NR1 | 0 | 100 | 0 | 1.3 | 2 | 2.5 | 1.9 | 1 |
| IR1 | 100 | 0 | 0 | 1.3 | 2 | 2.5 | 1.9 | 1 |
| NR6 | 0 | 100 | 50 | 1.3 | 2 | 2.5 | 1.9 | 1 |

NR1 Samples

Seven samples of material NR1 were cut into identical ASTM dumbbell shapes. The dumbbell shaped materials were stretched using an Instron 5567 machine to form seven samples having stretch ratios of 1, 2, 3, 3.5, 4, 5 and 6. After stretching, the length of the samples was about 80 mm and the width of the central part used for testing was about 4 mm. For each sample, a first body and a second body component of an apparatus was clamped to opposing surfaces of the central part of the stretched samples to hold the samples in a pre-determined stretched state having a select stretch ratio as generated in the sample by the Instron machine. The excess sample material extending outward from the outer perimeter of the first and second bodies was cut off with a razor. A first and second retaining member was positioned over the end portions of the first and second bodies to prevent the bodies from separating and secure the sample material in a stretched state between the bodies. The clamps were removed and the assembled apparatus containing the sample was inserted into an NMR rotor insert for testing. The rotor had an inner diameter of 5 mm and a length of 13 mm.

Figure 4:
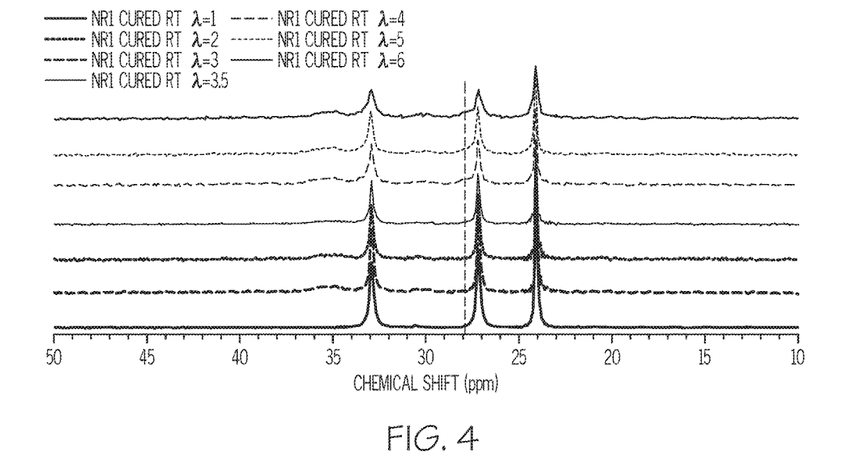
FIG. 4 shows an NMR spectrum, $^{13}C$ direct polarization-MAS, for samples at stretching ratios of 1, 2, 3, 3.5, 4, 5 and 6.

A Bruker Avance Ultrashield 300 spectrometer equipped with a 7 mm diameter magic angle spinning (MAS) rotor was used to obtain the NMR spectrums. Each NR1 sample was rotated at the magic angle of 54.74° with respect to the external magnetic field with the NMR device at room temperature at a sample spinning frequency of 4 kHz, with a recycle delay of 20 seconds. A solid-state $^{13}C$ direct polarization-NMR spectrum as a function of stretching ratio was measured under a $^1H$ dipolar decoupling condition with a field strength of 29.4 kHz at room temperature for each NR1 sample. FIG. 4 shows the $^{13}C$ direct polarization-MAS spectrums for the NR1 samples at stretching ratios of 1, 2, 3, 3.5, 4, 5 and 6. As shown, a peak appeared at about 28 ppm, represented by the vertical dotted line, ad beginning at a stretch ratio of about 3 a crystalline arrangement in the NR1 samples was induced by stretching. The intensity of the crystalline peak increased as the stretch ratio increased.

IR1 Samples

Two samples of material IR1 were cut into identical ASTM dumbbell shapes. The dumbbell shaped materials were stretched using an Instron 5567 machine to form two samples having stretch ratios of 4 and 5. The stretched IR1 samples were prepared in an apparatus and tested in an NMR device in the same manner as described above for the NR1 samples.

Figure 5:
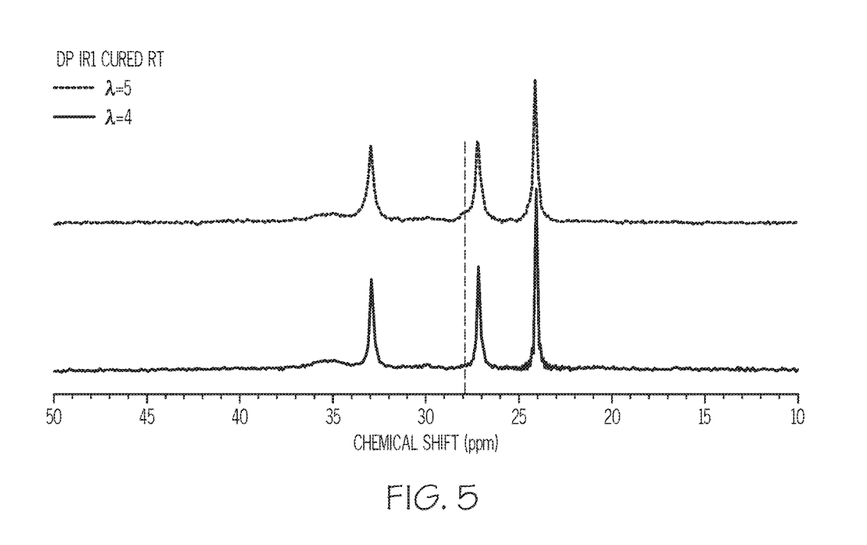
FIG. 5 shows an NMR spectrum, $^{13}C$ direct polarization-MAS, for samples at stretching ratios of 4 and 5.

A $^{13}C$ direct polarization-NMR spectrum as a function of stretching ratio was obtained for each IR1 sample. FIG. 5 shows the $^{13}C$ direct polarization-MAS spectrums for the IR1 samples at stretching ratios of 4 and 5. As shown, a peak appeared at about 28 ppm, represented by the vertical dotted line, and beginning at a stretch ratio of about 4 a crystalline arrangement in the IR1 samples was induced by stretching the samples. The intensity of the crystalline peak increased as the stretch ratio increased.

NR6 Samples

Five samples of material NR6 were cut into identical ASTM dumbbell shapes. The dumbbell shaped materials were stretched using an Instron 5567 machine to form five samples having stretch ratios of 1, 2, 3, 4 and 5. The stretched NR6 samples were prepared in an apparatus and tested in an NMR device in the same manner as described above for the NR1 samples.

Figure 6:
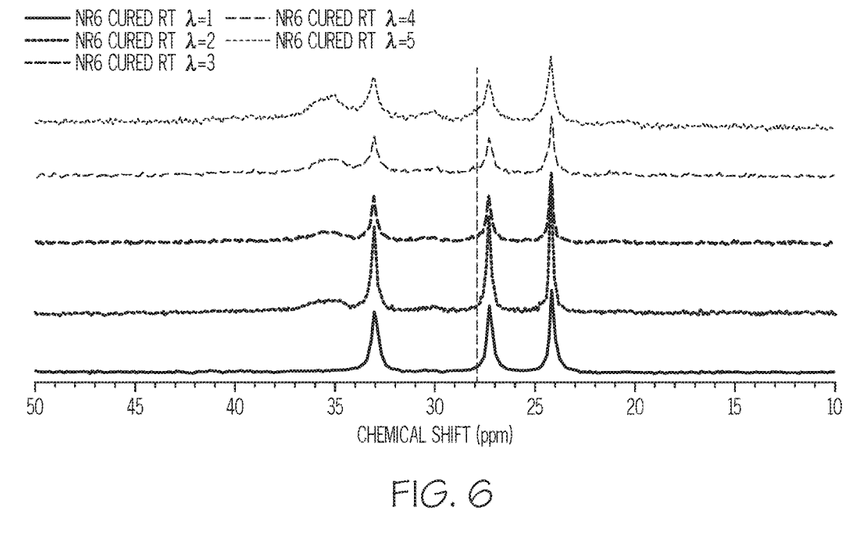
FIG. 6 shows an NMR spectrum, $^{13}C$ direct polarization-MAS, for samples at stretching ratios of 1, 2, 3, 4 and 5.

A $^{13}C$ direct polarization-NMR spectrum as a function of stretching ratio was obtained for each NR6 sample. FIG. 6 shows the $^{13}C$ direct polarization-MAS spectrums for the NR6 samples at stretching ratios of 1, 2, 3, 4 and 5. As shown, a peak appeared at about 28 ppm, represented by the vertical dotted line, and beginning at a stretch ratio of about 3 a crystalline arrangement in the NR6 samples was induced by stretching the samples. The intensity of the crystalline peak increased as the stretch ratio increased.

Strain-Induced Crystalline Material

Figure 7:
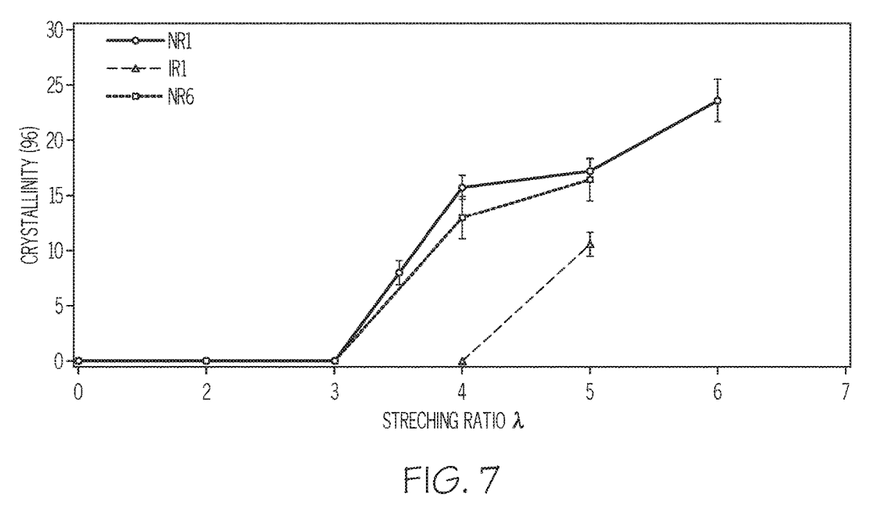
FIG. 7 shows the percentage of crystalline material present in the samples of FIGS. 4, 5 and 6 versus stretching ratios.

The stain-induced crystallinity of all of the samples (NR1, IR1 and NR6) was analyzed as a function of stretching ratio. The percentage of crystallinity of all of the samples (the ratio of integral of the crystalline peak over the sum of integrals of the crystalline and amorphous peaks) as function of the stretching ratio is provided in FIG. 7.

The measured crystallinity indicates that natural rubber crystallizes at reduced stretching ratios as compared to isoprene rubber. This result is consistent with reported observations in literature.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. An apparatus for testing a sample with NMR comprising: a. a first body comprising a sample contact surface along its length and a second body comprising a sample contact surface along its length for holding a sample comprising a stretched elastomer having a pre-determined stretch ratio; b. the sample arranged between the contact surface of the first body and the contact surface of the second body, wherein the sample contact surface of the first body and the sample contact surface of the second body press on the sample; c. a retaining member positioned around a portion of the sample, the portion of the sample arranged between a portion of the first body and a portion of the second body, wherein the retaining member secures the sample pressed between the first body and the second body.

2. The apparatus of claim 1, the sample being a stretched sample of an elastomer.

3. The apparatus of claim 1, the sample having a stretch ratio of greater than 4.

4. The apparatus of claim 1, the sample containing rubber.

5. The apparatus of claim 1, the first body and the second body being in direct contact with the sample.

6. The apparatus of claim 1, the first body, the second body, or the retaining member being made of plastic.

7. The apparatus of claim 1, the plastic being a thermoplastic.

8. The apparatus of claim 1, the retaining member being positioned around the entire length of the first body and the second body.

9. The apparatus of claim 1, further comprising a second retaining member, the second retaining member being positioned around an end portion of the first body and an end portion of the second body.

10. The apparatus of claim 9, the first retaining member and the second retaining member being removably fixed to the first body and the second body.

11. The apparatus of claim 9, the first retaining member and the second retaining member having same shape and dimensions.

12. The apparatus of claim 1, the sample contact surface of the first body and the sample contact surface of the second body being in direct contact with the sample.

13. The apparatus of claim 1, the first body and the second body having the same shape and dimensions.

14. The apparatus of claim 1, wherein the sample being in a sample receiving space of an NMR device for rotating or analyzing the sample.

15. The apparatus of claim 14, a solid state NMR spectrum of the sample being measured while the sample is rotated by the NMR device.

16. The apparatus of claim 15, the sample being rotated in the NMR device at a frequency of 2 to 10 kHz.

17. The apparatus of claim 15, the sample being positioned parallel to the axis of rotation.

18. A method for analyzing the molecular structure of a sample comprising: a. introducing the apparatus of claim 1 into a sample receiving space of an NMR device; b. rotating the sample in the apparatus in the NMR device; c. obtaining a NMR spectrum of the sample; d. calculating the amount of strain-induced crystallinity in the sample for the pre-determined stretch ratio.

19. The method of claim 18, the sample being rotated in the NMR device at a frequency of 2 to 10 kHz.

20. The method of claim 18, the sample being rotated in the NMR device at the magic angle of 54.74.degree. with respect to the external magnetic field to detect an NMR spectrum.

21. The method of claim 18, the sample being a stretched sample of an elastomer.

22. The method of claim 18, the sample having a stretch ratio of greater than 4.

23. The method of claim 18, further comprising identifying strain-induced crystalline structure in the sample.

24. The method of claim 18, further comprising positioning the first body against a first surface of the sample and the second body against a second surface of the sample.

25. The method of claim 24, further comprising arranging a second retaining member over a portion of the first body and the second body.

26. The method of claim 18, further comprising portions of the stretched sample being arranged within a second retaining member.

27. The method of claim 18, further comprising the retaining member being positioned around the entire length of the first body and the second body.

28. The method of claim 18, the sample being positioned in the apparatus such that the sample is rotated parallel to the axis of rotation.

* * * * *